US009072618B2

(12) United States Patent
Doerr et al.

(10) Patent No.: US 9,072,618 B2
(45) Date of Patent: *Jul. 7, 2015

(54) BIOCORRODABLE IMPLANT IN WHICH CORROSION MAY BE TRIGGERED OR ACCELERATED AFTER IMPLANTATION BY MEANS OF AN EXTERNAL STIMULUS

(75) Inventors: Thomas Doerr, Berlin (DE); Alexander Borck, Aurachtal (DE)

(73) Assignee: BIOTRONIK AG, Buelach (CH)

( * ) Notice: Subject to any disclaimer, the term of this patent is extended or adjusted under 35 U.S.C. 154(b) by 133 days.

This patent is subject to a terminal disclaimer.

(21) Appl. No.: 13/085,718

(22) Filed: Apr. 13, 2011

(65) Prior Publication Data

US 2011/0276124 A1   Nov. 10, 2011

Related U.S. Application Data

(60) Provisional application No. 61/331,868, filed on May 6, 2010.

(51) Int. Cl.
*A61F 2/82* (2013.01)
*A61L 27/52* (2006.01)
(Continued)

(52) U.S. Cl.
CPC . *A61F 2/82* (2013.01); *A61L 27/52* (2013.01); *A61F 2210/0066* (2013.01); *A61F 2210/0004* (2013.01); *A61F 2210/0061* (2013.01); *A61F 2210/009* (2013.01); *A61F 2250/0001* (2013.01);
(Continued)

(58) Field of Classification Search
CPC ................ A61F 2210/0061; A61F 2210/0066; A61F 2250/0001; A61F 2/82; A61F 31/148; A61F 2210/0004; A61F 2250/003; A61L 27/28; A61L 27/52; A61L 27/58; A61L 31/08; A61L 31/14; A61L 27/04; A61L 27/47; A61L 31/022
USPC ................... 604/20; 623/1.38–1.48
See application file for complete search history.

(56) References Cited

U.S. PATENT DOCUMENTS 6,585,765 B1 *   7/2003   Hossainy et al. ............. 623/1.45
6,833,004 B2 *  12/2004   Ishii et al. .................... 623/1.15
(Continued)

FOREIGN PATENT DOCUMENTS

WO    2006108065 A2    12/2006
WO    2008036554 A2     3/2008

OTHER PUBLICATIONS

European Search Report for Parent Application No. EP 11 16 2224.

*Primary Examiner* — Andrew Iwamaye
(74) *Attorney, Agent, or Firm* — Wagenknecht IP Law Group PC

(57) ABSTRACT

The present invention relates to a biocorrodable implant in which corrosion may be triggered or accelerated after implantation by applying an external stimulus, the implant having a base body which is completely or partially composed of a biocorrodable metallic material, and the base body having a coating with a protective layer which is not biocorrodable. According to the invention, the implant has control elements which are configured in such a way that the protective layer, optionally in combination with the control elements, completely or partially encloses the base body so as to be impermeable to bodily medium, and the protective layer being convertible to a form which is permeable to bodily medium as the result of a change in shape of the control elements which may be regulated and/or controlled by an external stimulus.

11 Claims, 5 Drawing Sheets

(51) Int. Cl.

| | | |
|---|---|---|
| *A61L 27/04* | (2006.01) | |
| *A61L 27/28* | (2006.01) | |
| *A61L 27/50* | (2006.01) | |
| *A61L 27/58* | (2006.01) | |
| *A61L 31/02* | (2006.01) | |
| *A61L 31/08* | (2006.01) | |
| *A61L 31/14* | (2006.01) | |

(52) U.S. Cl.
CPC .......... *A61F 2250/003* (2013.01); *A61L 27/04* (2013.01); *A61L 27/28* (2013.01); *A61L 27/50* (2013.01); *A61L 27/58* (2013.01); *A61L 31/022* (2013.01); *A61L 31/08* (2013.01); *A61L 31/14* (2013.01); *A61L 31/148* (2013.01)

(56) References Cited

U.S. PATENT DOCUMENTS

| | | | |
|---|---|---|---|
| 7,041,130 B2 * | 5/2006 | Santini et al. | 623/1.42 |
| 7,172,622 B2 * | 2/2007 | Weber et al. | 623/1.12 |
| 7,223,282 B1 * | 5/2007 | Hossainy | 623/1.15 |
| 7,329,431 B2 * | 2/2008 | Ishii | 427/2.24 |
| 7,384,660 B2 * | 6/2008 | Hossainy et al. | 427/2.25 |
| 7,601,382 B2 * | 10/2009 | Weber et al. | 427/2.1 |
| 7,985,252 B2 * | 7/2011 | Radhakrishnan et al. | 623/1.46 |
| 8,002,821 B2 * | 8/2011 | Stinson | 623/1.38 |
| 2003/0021762 A1 * | 1/2003 | Luthra et al. | 424/78.32 |
| 2003/0033004 A1 * | 2/2003 | Ishii et al. | 623/1.15 |
| 2003/0083646 A1 * | 5/2003 | Sirhan et al. | 604/891.1 |
| 2003/0190406 A1 * | 10/2003 | Hossainy et al. | 427/2.25 |
| 2005/0186241 A1 * | 8/2005 | Boyle et al. | 424/423 |
| 2006/0217798 A1 * | 9/2006 | Santini et al. | 623/1.42 |
| 2006/0229711 A1 * | 10/2006 | Yan et al. | 623/1.38 |
| 2007/0141106 A1 * | 6/2007 | Bonutti et al. | 424/423 |
| 2007/0191937 A1 * | 8/2007 | Hossainy | 623/1.42 |
| 2007/0191938 A1 * | 8/2007 | Hossainy | 623/1.42 |
| 2007/0231363 A1 * | 10/2007 | Chen et al. | 424/423 |
| 2008/0071358 A1 * | 3/2008 | Weber et al. | 623/1.42 |
| 2008/0188836 A1 * | 8/2008 | Weber et al. | 604/890.1 |
| 2008/0199510 A1 | 8/2008 | Ruane et al. | |
| 2009/0264975 A1 * | 10/2009 | Flanagan et al. | 623/1.2 |
| 2010/0023112 A1 * | 1/2010 | Borck et al. | 623/1.15 |
| 2010/0023116 A1 * | 1/2010 | Borck et al. | 623/1.42 |
| 2010/0070013 A1 * | 3/2010 | Park | 623/1.11 |
| 2011/0153004 A1 * | 6/2011 | Kleiner et al. | 623/1.43 |
| 2011/0245914 A1 * | 10/2011 | Santini et al. | 623/1.42 |
| 2012/0185024 A1 * | 7/2012 | Hauer et al. | 607/116 |

* cited by examiner

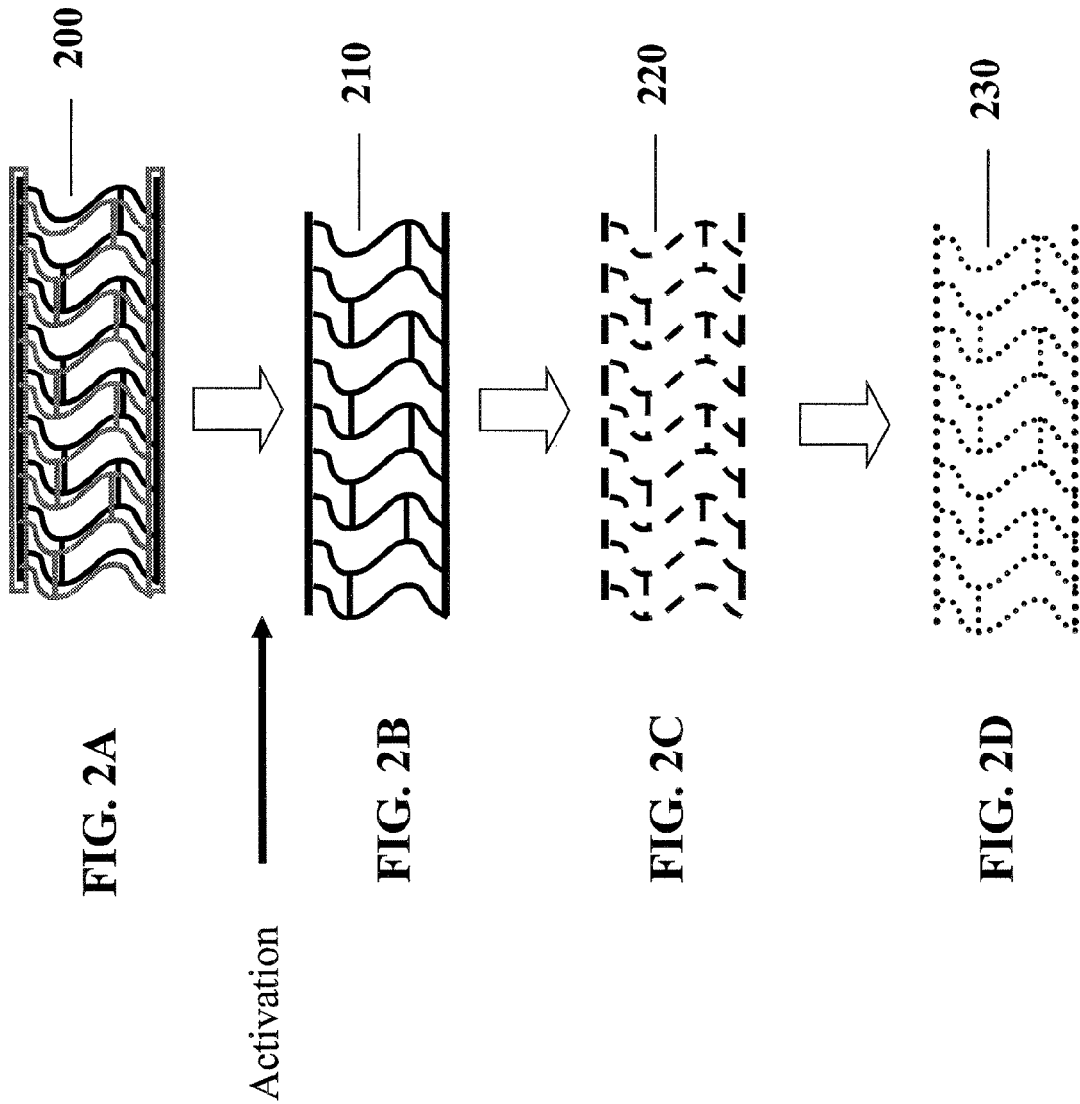

BIOCORRODABLE IMPLANT IN WHICH CORROSION MAY BE TRIGGERED OR ACCELERATED AFTER IMPLANTATION BY MEANS OF AN EXTERNAL STIMULUS

CROSS REFERENCE TO RELATED APPLICATIONS

This invention claims benefit of priority to U.S. patent application Ser. No. 61/331,868, filed on May 6, 2010; the contents of which are herein incorporated by reference in their entirety.

TECHNICAL FIELD

The invention relates to a biocorrodable implant such as a vascular support or an orthopedic implant, and more specifically to a biocorrodable implant in which corrosion may be triggered or accelerated after implantation by means of an external stimulus.

BACKGROUND

Implants have found use in modern medical technology in many different embodiments. They are used, for example, for supporting and/or bracing vessels, hollow organs, and duct systems (endovascular implants, for example stents), for attaching and temporarily fixing tissue implants and tissue transplants, as well as for orthopedic purposes, for example as pins, plates, or screws. Frequently, only a temporary supporting or retaining function is necessary or desired until the healing process is complete or the tissue has stabilized. To avoid complications resulting from the implant permanently residing in the body, either the implants must be surgically removed, or they are composed of a material which is gradually degraded in the body, i.e., is biocorrodable. The number of biocorrodable materials based on polymers or alloys is constantly increasing. Biocorrodable metal alloys of the elements magnesium, iron, and tungsten, among others, are known. One form of implant used particularly often is the stent.

The implantation of vascular supports such as stents, for example, has become established as one of the most effective therapeutic measures in the treatment of vascular diseases. Stents perform a support function in hollow organs of a patient. For this purpose, stents of conventional design have a filigreed support structure made of metallic braces, which are initially in a compressed form for insertion into the body, and are then expanded at the site of application. One of the main fields of application of such stents is to permanently or temporarily widen and keep open vascular constrictions, in particular constrictions (stenoses) of the coronary vessels. In addition, aneurysm stents, for example, used for supporting damaged vascular walls are known.

Stents have a circumferential wall of sufficient load capacity to keep the constricted vessel open to the desired extent, and have a tubular base body through which blood flows through unhindered. The circumferential wall is generally formed by a lattice-like support structure which allows the stent to be inserted in a compressed state, with a small outer diameter, up to the constriction in the particular vessel to be treated, and at that location, for example by use of a balloon catheter, to be expanded until the vessel has the desired enlarged inner diameter. The process of positioning and expanding the stent during the procedure and the subsequent location of the stent in the tissue after the procedure is completed must be monitored by the cardiologist. This may be achieved using imaging methods such as X-ray analysis, for example.

The stent has a base body made of an implant material. Such an implant material is a nonliving material which is used for medical applications and interacts with biological systems. The basic requirement for use of a material as an implant material, which when properly used is in contact with the bodily surroundings, is compatibility with the body (biocompatibility). Biocompatibility is understood to mean the ability of a material to induce an appropriate tissue reaction in a specific application. This includes adaptation of the chemical, physical, biological, and morphological surface characteristics of an implant to the recipient tissue, with the objective of a clinically sought interaction. The biocompatibility of the implant material is also dependent on the time sequence of the reaction of the biosystem which has received the implant. Relatively short-term irritation and inflammation occur which may result in changes in the tissue. Accordingly, biological systems react in various ways, depending on the characteristics of the implant material. The implant materials may be divided into bioactive, bioinert, and degradable/absorbable materials, depending on the reaction of the biosystem.

Implant materials for stents include polymers, metallic materials, and ceramic materials (as a coating, for example). Biocompatible metals and metal alloys for permanent implants contain, for example, stainless steels (316L, for example), cobalt-based alloys (CoCrMo cast alloys, CoCrMo forged alloys, CoCrWNi forged alloys, and CoCrNiMo forged alloys, for example), pure titanium and titanium alloys (CP titanium, TiAl6V4, or TiAl6Nb7, for example), and gold alloys. For biocorrodable stents, the use of magnesium or pure iron, or biocorrodable base alloys of the elements magnesium, iron, zinc, molybdenum, and tungsten, is recommended. Thus, for example, DE 197 31 021 A1 proposes the production of medical implants from a metallic material whose primary component is iron, zinc, or aluminum, or an element from the group of alkali metals or alkaline earth metals. Alloys based on magnesium, iron, and zinc are described as particularly suitable. Secondary components of the alloys may be manganese, cobalt, nickel, chromium, copper, cadmium, lead, tin, thorium, zirconium, silver, gold, palladium, platinum, silicon, calcium, lithium, aluminum, zinc, and iron. Also known from DE 102 53 634 A1 is the use of a biocorrodable magnesium alloy containing >90% magnesium, 3.7-5.5% yttrium, 1.5-4.4% rare earth metals, and the remainder <1%, which is particularly suitable for producing an endoprosthesis, for example in the form of a self-expanding or balloon-expandable stent. The use of biocorrodable metallic materials in implants may result in a considerable reduction in rejection or inflammatory reactions. Such biocorrodable implants and stents frequently also have a coating or cavity filling with a suitable polymer. Also known are stents made of biocorrodable polymers such as polylactide (PLA), poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, polyhydroxybutyrate (polyhydroxybutyric acid/PHB), polyanhydride, polyphosphoesters, polyamino acids, poly(alpha-hydroxy acid), or related copolymer materials.

One problem with biocorrodable implants, in particular biocorrodable stents, is the difficulty in ensuring a service life which is long enough to achieve the desired medical effect. As a rule, the implant begins to corrode immediately after implantation. Coatings, preferably self-biocorrodable coatings, are known which may retard such a biocorrosion process. However, even for a retarded biocorrosion process the loss of stability or integrity of the implant begins shortly after the implantation, causing the implant to become increasingly unstable over time. Ensuring the stability or integrity of a biocorrodable implant over the desired service life essentially without impairment, and having a biocorrosion process of the implant begin to an appreciable extent only after the end of the desired service life, are currently not possible.

The object of the present invention is to reduce or avoid at least one of the disadvantages of the prior art.

SUMMARY OF THE INVENTION

This object is achieved by providing a biocorrodable implant in which corrosion may be triggered or accelerated after implantation by means of an external stimulus, the implant having a base body which is completely or partially composed of a biocorrodable metallic material, and the base body having a coating with a protective layer which is not biocorrodable, characterized in that the implant has control elements which are configured in such a way that the protective layer, optionally in combination with the control elements, completely or partially encloses the base body so as to be impermeable to bodily medium, and the protective layer being convertible to a form which is permeable to bodily medium as the result of a change in shape of the control elements which may be regulated and/or controlled by an external stimulus.

DESCRIPTION OF THE DRAWINGS

FIG. 2A-2D show the sequence of the biocorrosion of a stent according to the invention after implantation.

DETAILED DESCRIPTION

Figure 1A:
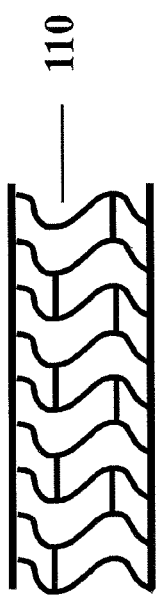
FIG. 1A-1C show the sequence of the biocorrosion of a stent of the prior art after implantation.

The invention provides a biocorrodable implant in which corrosion may be triggered or accelerated after implantation by means of an external stimulus, the implant having a base body which is completely or partially composed of a biocorrodable metallic material, and the base body having a coating with a protective layer which is not biocorrodable, characterized in that the implant has control elements which are configured such that the protective layer, optionally in combination with the control elements, completely or partially encloses the base body so as to be impermeable to bodily medium, and the protective layer being convertible to a form which is permeable to bodily medium as the result of a change in shape of the control elements which may be regulated and/or controlled by an external stimulus.

In the following description and within the meaning of the invention, "bodily medium" refers to all media naturally or unnaturally present in the body. These include liquids containing water, for example blood, lymph fluid, and saliva, hydrogen, oxygen, nitrogen, carbon dioxide, ions, and ion solutions containing phosphate or calcium, for example.

The implant according to the invention is characterized in that after implantation the protective layer protects the implant from uncontrolled biocorrosion. The base body of the implant is not accessible or induced to undergo corrosion until an external stimulus is administered, for example by supplying external energy, for example from an external (ex vivo) source. Thus, the corrosion characteristics of the implant according to the invention after implantation may be externally controlled and/or regulated by controlling the external stimulus. For this purpose the implant has control elements which, when triggered by an external stimulus, are able to undergo a predefined change in shape. The control elements are designed and configured in such a way that the implant is initially enclosed by the protective layer, optionally in combination with the control elements, so as to be impermeable to bodily medium. When a change in shape of the control elements is caused by administration of an external stimulus, the base body of the implant is no longer tightly sealed against bodily medium, and becomes accessible to the bodily medium so that a biocorrosion process may then begin or be accelerated.

The implant according to the invention is preferably a stent.

The implant according to the invention has a base body which is completely or partially composed of a biocorrodable material. The implant preferably has a base body which is completely or partially composed of a biocorrodable metallic or polymeric material. In particular, the biocorrodable metallic material may contain or be composed of magnesium, a biocorrodable magnesium alloy, pure iron, a biocorrodable iron alloy, a biocorrodable tungsten alloy, a biocorrodable zinc alloy, or a biocorrodable molybdenum alloy.

The term "biocorrodable" within the meaning of the invention refers to substances, materials, alloys, and elements in which degradation/conversion takes place in the physiological surroundings, so that the portion of the implant composed of the material is completely or predominantly no longer present.

In the present context, a magnesium alloy, iron alloy, zinc alloy, molybdenum alloy, or tungsten alloy is understood to mean a metallic structure whose primary component is magnesium, iron, zinc, molybdenum, or tungsten, respectively. The primary component is the alloy component having the highest proportion by weight in the alloy. A proportion of the primary component is preferably greater than 50% by weight, in particular greater than 70% by weight. Secondary components of the alloys may be manganese, cobalt, nickel, chromium, copper, cadmium, lead, tin, thorium, zirconium, silver, gold, palladium, platinum, silicon, calcium, lithium, aluminum, zinc, and iron. The composition of the alloy is to be selected so that the alloy is biocorrodable. Particularly suitable biocorrodable magnesium alloys are disclosed in DE 102 53 634 A1, and include a biocorrodable magnesium alloy having proportions of magnesium >90%, yttrium 3.7-5.5%, rare earth metals 1.5-4.4%, and the remainder <1%. This magnesium alloy is particularly well suited for manufacturing an endoprosthesis, for example in the form of a self-expanding or balloon-expandable stent.

Artificial plasma as specified under EN ISO 10993-15: 2000 for biocorrosion testing (composition: NaCl 6.8 g/L, $CaCl_2$ 0.2 g/L, KCl 0.4 g/L, $MgSO_4$ 0.1 g/L, $NaHCO_3$ 2.2 g/L, $Na_2HPO_4$ 0.126 g/L, $NaH_2PO_4$ 0.026 g/L) is used as test medium for testing the corrosion characteristics of a particular material. For this purpose, a sample of the materials to be tested is kept at 37° C. in a sealed sample container containing a defined quantity of the test medium. The samples are withdrawn at time intervals of a few hours to several months, depending on the anticipated corrosion characteristics, and analyzed in a known manner for signs of corrosion. The artificial plasma according to EN ISO 10993-15:2000 corresponds to a medium that is similar to blood, thus providing an opportunity to reproducibly duplicate a physiological environment within the meaning of the invention. A substance is referred to as nonbiocorrodable, for example, if it has corroded or reacted by no more than 50% in the above-referenced test after a period of 12 months.

A protective layer within the meaning of the invention is a coating applied, at least in places, to the base body of the implant. The entire surface of the base body of the implant is preferably covered by the coating. A layer thickness of the protective layer is preferably in the range of 1 nm to 100 particularly preferably 300 nm to 15 μm. The protective layer may be applied directly to the implant surface, or one or more additional layers may be provided between the implant surface and the protective layer. Such an additional layer may, for example, be an adhesive layer which improves the adhesion of the protective layer. The processing may be carried out according to standard methods for the coating. Single-layer as well as multilayer systems may be produced. In particular, the implant according to the invention may be characterized in that an additional layer is provided between the base body and the protective layer which improves the adhesion of the protective layer.

The protective layer is not biocorrodable, and may contain or be composed of a variety of known materials and polymers. For example, the protective layer may contain or be composed of poly-L-lactide or another representative of polyesters such as PDLLA, PLGA, P3HB, P4HB, or mixtures or copolymers thereof. Alternatively or additionally, the protective layer may contain parylene (parylene C or other derivatives), preferably in the form of parylene with so-called "pin holes." Additionally or alternatively, the protective layer may contain cellulose, preferably as a film, such as nitrocellulose, methylcellulose, or carboxymethylcellulose, for example. The protective layer may also contain polyvinyl alcohols, wherein film formation may be optimized by selection of the molar mass and the deacetylation rate. Polyvinyl alcohol is a crystalline polymer having a low degree of branching on account of its preparation method. Polyvinyl acetate is prepared from vinyl acetate. The polyvinyl acetate is hydrolyzed to form the polyvinyl alcohol by reaction with bases. The melting temperature and glass transition temperature depend not only on the hydrolysis rate and molar mass, but also on the distribution of the acetyl groups (statistically or in blocks), the tacticity, and the water content of the polymer. Polyvinyl alcohols having moderate to high hydrolysis rates and polymerization rates up to 2000 are suitable. The films produced from polyvinyl alcohol are tear-resistant and viscoplastic, and oil- and heat-resistant. Polyalcohols such as glycerin and ethylene glycol, for example, may be used as softener.

The protective layer, optionally in combination with the control elements, encloses the base body so as to be completely or partially impermeable to bodily medium, so that the parts of the base body which are enclosed are not directly contactable by bodily medium.

For this purpose the protective layer may be present as an unperforated coating which is impermeable to bodily medium and which completely or partially encloses the base body of the implant. In this case the control elements are preferably mounted on, in, or under the protective layer, so that the integrity and seal-tightness of the protective layer against contact with bodily medium may be impaired by a change in the shape of the control elements and degraded in such a way that parts of the base structure which are originally impermeably enclosed by the protective layer may then be contacted by bodily medium.

In another embodiment the protective layer is present as a perforated coating or membrane, control elements being situated in the perforation openings in such a way that the protective layer in combination with the control elements initially completely or partially encloses the base body of the implant so as to be impermeable to bodily medium. In this case the control elements are situated on or in the protective layer, so that the integrity and seal-tightness of the protective layer against bodily medium may be impaired by a change in shape of the control elements and degraded in such a way that parts of the base structure originally enclosed by the protective layer may then be contacted by bodily medium.

The implant according to the invention is designed in such a way that a change in shape of the control elements may be regulated and/or controlled by an external stimulus. The external stimulus may directly cause the change in shape of the control elements, or may act on the implant in such a way that a signal is indirectly generated which triggers or causes the change in shape of the control elements. The external stimulus may, for example, include or be composed of a temperature change, electromagnetic radiation, high-frequency radiation (RF), an ultrasound signal, ionizing radiation, a magnetic field, and/or light in various spectral ranges. Suitable sources for generating such an external stimulus are known to one skilled in the art. Such sources may include devices for administering one or more of the aforementioned external stimuli, for example for administering ultrasound energy, preferably high-intensity focused ultrasound (HIFU) energy, or for administering high-frequency radiation or ionizing radiation, or magnetic fields. Suitable magnetic fields may be generated and provided by MRT devices.

In one special embodiment the implant is designed in such a way that a change in temperature may be induced in the implant as a result of the external stimulus. In addition to the direct application of thermal energy, such a change in temperature in the implant may be achieved, for example, by irradiating the base body of the implant with high-frequency radiation or by applying a magnetic field.

The protective layer of the implant may contain means which allow an external stimulus to be converted to a change in temperature. For this purpose the protective layer may contain magnetic particles, for example, which are set into vibration by applying suitable alternating magnetic fields which may cause a change in temperature in the implant.

The implant according to the invention has control elements which may undergo a change in shape which may be regulated and/or controlled by an external stimulus. Such a change in shape is understood to mean a measurable change in the external appearance of the control element which is not limited to the general thermal expansion of a body as the result of a temperature increase. Such control elements preferably contain or are composed of polymeric materials having the desired characteristics. Such polymeric materials are known to one skilled in the art. Control elements are preferably used in which the change in shape may be triggered by a change in temperature.

In one preferred embodiment the implant contains control elements which include or are composed of a hydrogel. A hydrogel is a polymer which contains water but which is insoluble in water, and whose molecules are linked chemically, for example by covalent or ionic bonds, or physically, for example by interconnection of the polymer chains, to form a three-dimensional network. Hydrogels according to the invention are able to undergo a change in volume as a reaction to an external stimulus due to the fact that they have a variable swelling capability and are thus able to absorb various quantities of water per mmol of hydrogel polymer in a regulatable and/or controllable manner. These hydrogels may be prepared, for example, by reacting ethylenically unsaturated monomers and polymers containing ionizable groups with crosslinkers and polymerization catalysts. Alternatively, suitable hydrogels may be prepared by condensation reactions with difunctional and multifunctional monomers. Suitable monomers and polymers as well as methods for their preparation are known to one skilled in the art. Likewise, one skilled in the art is familiar with methods and processes for preparing suitable hydrogels using such monomers and/or polymers. Preferred hydrogels contain a polymer based on acrylamide, methacrylamide, dimethylaminoethyl methacrylates, or a derivative of acrylamide, methacrylamide, or dimethylaminoethyl methacrylates. Other preferred hydrogels contain a polymer based on poly-N-isopropylacrylamides and/or poly-N-isopropylacrylamide-co-allylamine and/or poly-N-isopropylamide (PNiPAM), or mixtures thereof with poly(p-dioxanone) as the hard segment.

Within the meaning of the invention, the term "swelling capability" refers to the property of the hydrogel to absorb a given quantity of water per mmol hydrogel polymer. A decreased swelling capability results in a reduction of the volume of the hydrogel, and thus a change in shape of the hydrogel or a control element containing such a hydrogel. Suitable methods and measuring processes for determining the swelling capability are known to one skilled in the art; measuring processes which have proven successful in the pharmaceutical sector are particularly suitable.

It is preferred to use hydrogels whose swelling capability is a function of temperature. Particularly preferred hydrogels have a reduced swelling capability with increasing temperature. Such hydrogels may be characterized in that their swelling capability decreases by at least 30%, preferably by up to 50%, particularly preferably by 30% to 50%, for a temperature increase of 10K.

The temperature dependency of the hydrogel is preferably set in such a way that it results in a pronounced hysteresis effect with regard to the swelling characteristics, so that the swelling capability remains reduced even upon a return to the starting temperature of 37° C.

As a result of the induced heating of the implant material the hydrogel is also heated, and its swelling characteristics are reduced to the extent that the change in shape of the hydrogel results in body fluids then being able to reach the biodegradable implant material and thus initiate the corrosion process.

In a further preferred embodiment the implant has control elements which contain or are composed of a shape memory polymer. Shape memory polymers are plastics which have a "shape memory" effect. A "shape memory" effect is understood to mean that a shape memory polymer may be stably converted from an original shape to another shape, in which it remains until the shape memory polymer returns to a previous or the original shape as a reaction to an external stimulus. When the implant has control elements containing a shape memory polymer, the shape memory polymer may be present as an essentially planar molded body, the molded body being convertible to a curved shape, for example, as the result of an external stimulus. For the transition of the shape memory polymer from the planar to the curved shape, the protective layer may be perforated, and the corrosion process may be triggered for the underlying base structure of the implant.

The invention is explained in greater detail below with reference to the following exemplary embodiments.

Figure 1B:
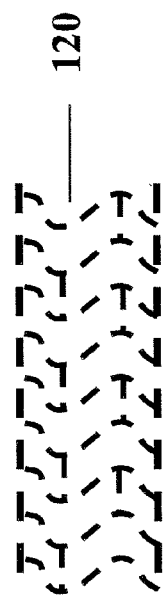
Figure 1C:
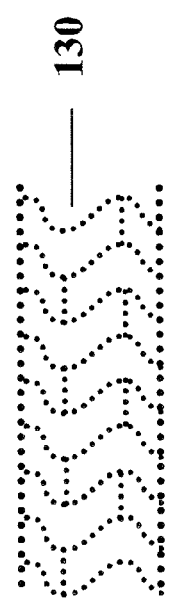

FIG. 1 illustrates the sequence of biocorrosion of a biocorrodable medical implant of the prior art after implantation, using the example of a stent. As shown in FIGS. 1A and 1B, the corrosion begins immediately after implantation 110, i.e., at the start of the service life, and proceeds essentially continuously according to the selected alloy characteristics. In a relatively early stage 120 the mechanical properties of the implant are markedly impaired (see FIGS. 1B and 1C), the degree of impairment also depending on the individual conditions in the tissue of the recipient. The desired, essentially complete degradation of the implant is represented in the later stage (130).

In contrast, FIGS. 2A through 2D illustrates the sequence of biocorrosion of a biocorrodable implant according to the invention, using the example of a stent after implantation. For implantation 200 the stent is coated with a nonbiodegradable protective layer (polymer or biocompatible wax, for example). This protective layer is perforated by an external stimulus (activation) only when the support function of the stent is no longer needed, thus initiating the process of corrosion 210. In this case, materials or material combinations may be used for the base structure of the implant which degrade in a relatively short time, such as magnesium alloys, for example, so that the time between loss of the support function 220 and complete degradation 230 may be kept as short as possible.

Figure 3:
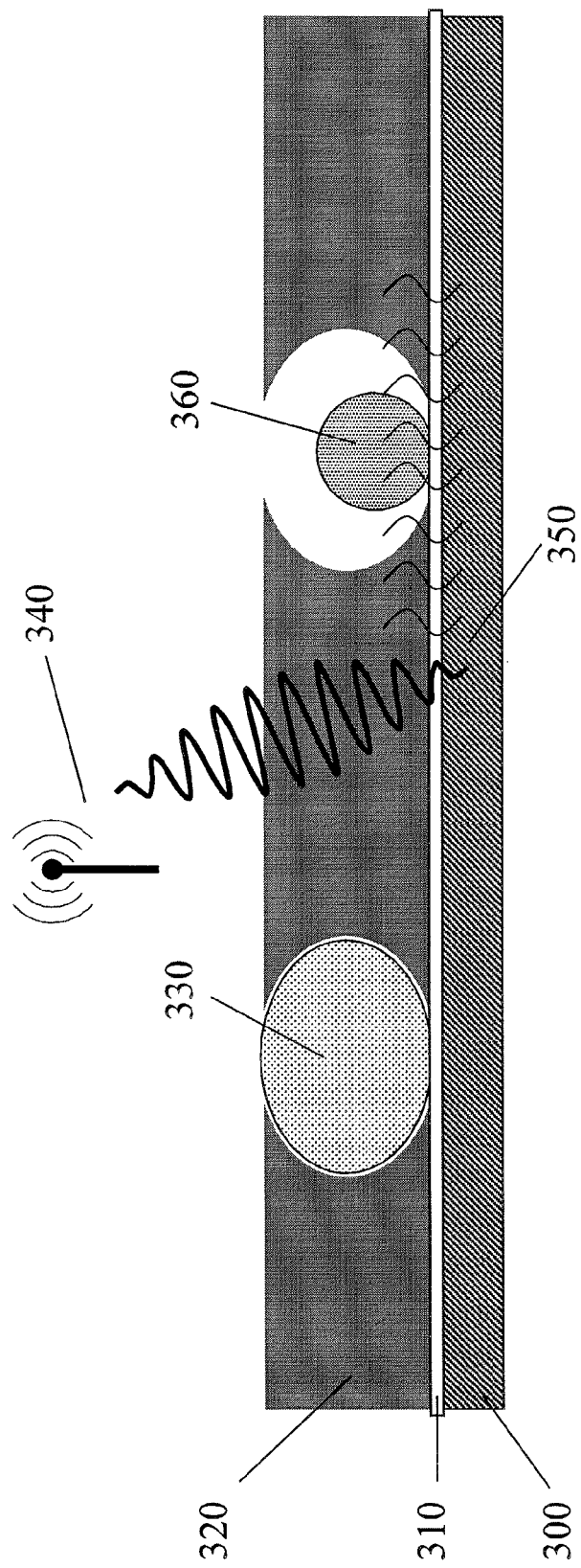
FIG. 3 shows a schematic illustration of a first embodiment of an implant according to the invention.

FIG. 3 schematically illustrates a first exemplary embodiment of an implant according to the invention. A protective layer in the form of a perforated membrane 320 is applied to the biodegradable material 300 of the implant, using a bonding agent 310. The perforation openings in the membrane 320 are sealed using a hydrogel 330. The hydrogel 330 used has a temperature-dependent swelling capability which decreases by approximately 30-50% when heated by 10K. The temperature dependency of the hydrogel 330 is preferably set in such a way that it results in a pronounced hysteresis effect with regard to the swelling characteristics, so that the resulting change in shape is essentially maintained, even after being temporarily heated and then returning to the starting temperature of 37° C. Temporary heating of the implant may be induced by external application of high-frequency energy, using a high-frequency transmitter 340. In this system the wavelength of the high-frequency transmitter 340 is coordinated with the antenna geometry of the biodegradable material 300 of the implant, thus enabling effective heating. The induced heating of the implant material also results in heating of the hydrogel, and the swelling characteristics thereof are reduced to the extent that the hydrogel undergoes a change in shape to form a reduced hydrogel 360, which opens up the perforation opening in the membrane 320 to a degree which allows body fluids to reach the biodegradable material 300 of the implant, thus initiating the corrosion process.

Figure 4:
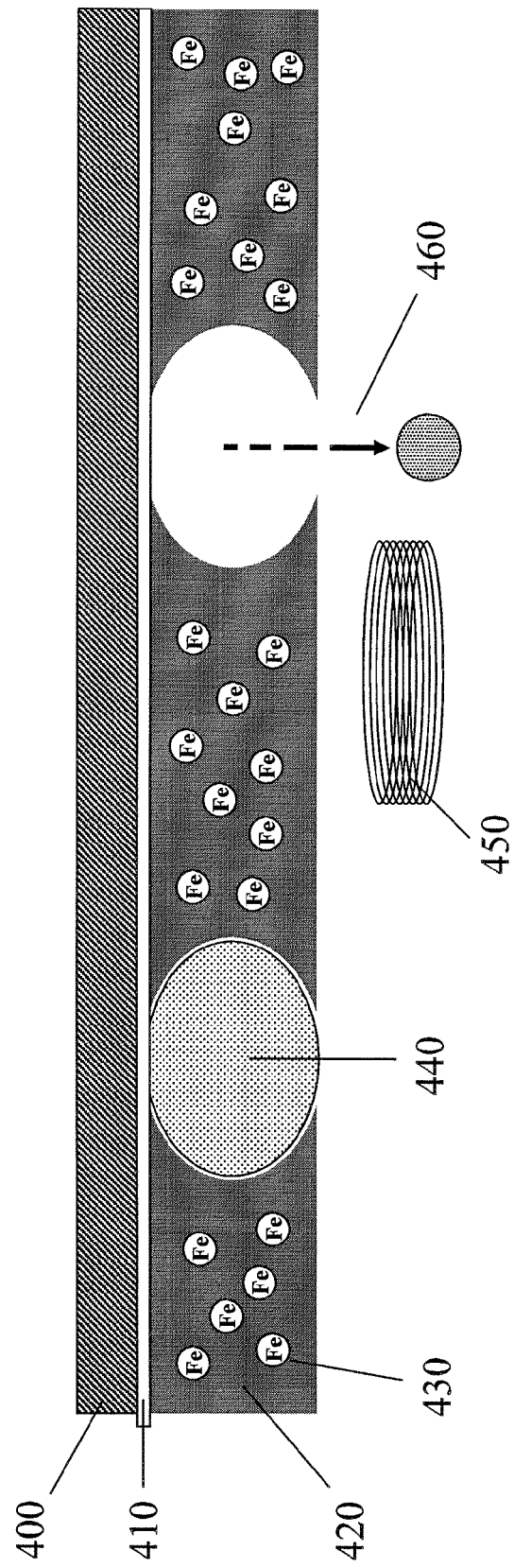
FIG. 4 shows a schematic illustration of a second embodiment of an implant according to the invention.

FIG. 4 schematically illustrates an alternative embodiment of the implant according to the invention. In this case a protective layer composed of a perforated membrane 420 is applied to the biodegradable material of the implant 400, using a bonding agent 410. This perforated membrane 420 contains magnetic nanoparticles 430. Here as well, the perforation openings are sealed using a hydrogel 440. In this embodiment a hydrogel 440 having a discontinuous swelling capability is used, and which above a given temperature (45°-50° C., for example) abruptly collapses to form a reduced hydrogel 460 and "falls out" of the perforation opening in the protective layer. In this case the membrane 420 is heated by an alternating magnetic field which is applied using an external magnetic alternating field generator 450. The magnetic nanoparticles 430 are set into vibration, thus heating the membrane 420 and the hydrogel 440.

Figure 5:
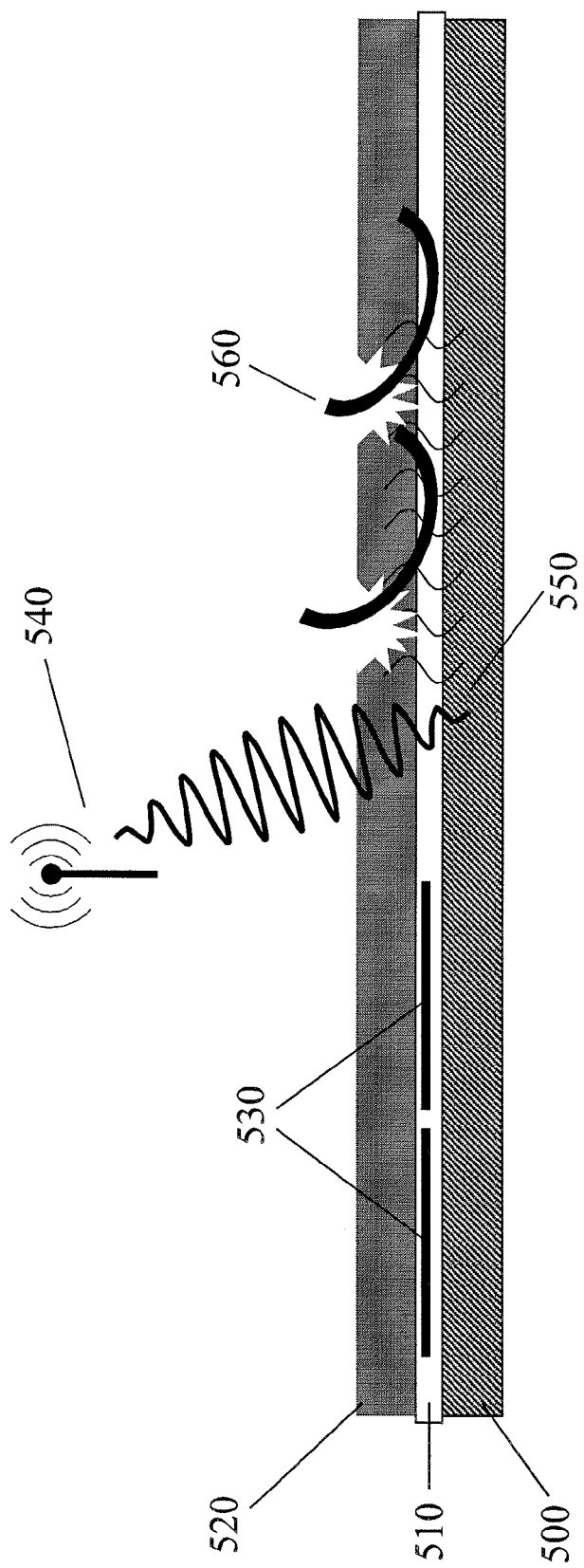
FIG. 5 shows a schematic illustration of a third embodiment of an implant according to the invention.

FIG. 5 schematically illustrates a further embodiment of the implant according to the invention. In this case a protective layer composed of an unperforated membrane 520 is applied to the biodegradable material of the implant 500, using a bonding agent 510. The bonding agent 510 also contains molded bodies 530 composed of a biocompatible, biodegradable shape memory polymer, wherein the original shape of this shape memory polymer is curved, and the linear, planar form of the molded body 530 represents the "deformed state" (set at 125° C.) of the shape memory polymer. The biodegradable implant material 500, and thus also the molded bodies 530, is heated to 45° C. for at least 10 seconds by applying high-frequency energy using an external high-frequency transmitter 540. The shape memory polymer of the molded bodies 530 once again assumes its original curved shape. The membrane 520 is perforated by the molded body 560, which at that point is changed in shape, and the corrosion process is initiated.

Alternatively, the change in shape of the shape memory polymer may be triggered by light. In one possible application, for example, a stent is subjected to angiographic follow-up examination, and depending on the findings the degradation of the stent is initiated by direct irradiation of the stent using an optical fiber catheter, using UV light having a wavelength less than 260 nanometers.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A biocorrodable implant system for triggering or accelerating corrosion of an implant after implantation, the implant system comprising:
    an implant comprising a base body which is completely or partially composed of a biocorrodable metallic material and adhered to the base body is a protective layer consisting of a perforated membrane and control elements positioned within the perforations, wherein the protective layer is not biocorrodable, wherein the control elements are made of a first material, the first material not forming a continuous layer above or below the perforated membrane; and
    an apparatus configured to transmit an external and ex vivo stimulus to the base body after implantation;
    characterized in that upon implantation, the control elements form a fluid tight seal with the perforations such that the protective layer is impermeable to bodily medium prior to transmission of the external and ex vivo stimulus, and a swelling capability of the control elements decreases in response to stimulation of the base body by the external and ex vivo stimulus to convert the protective layer to a form which is permeable to the bodily medium, thereby allowing the bodily medium to reach the base body to initiate corrosion of the base body.

2. The implant system according to claim 1, characterized in that the biocorrodable metallic material is a magnesium alloy.

3. The implant system according to claim 1, characterized in that the implant is a vascular support, a stent, or an orthopedic implant.

4. The implant system according to claim 1, characterized in that the external stimulus is selected from the group consisting of a temperature change, electromagnetic radiation, high-frequency radiation (RF), an ultrasound signal, ionizing radiation, a magnetic field, and light.

5. The implant system according to claim 1, characterized in that the external stimulus induces a change in temperature of the base body.

6. The implant system according to claim 1, characterized in that the decrease in swelling capability of the control elements is performed by regulating or controlling a change in temperature, electromagnetic radiation, or UV light.

7. The implant system according to claim 1, characterized in that the control elements comprise a hydrogel.

8. The implant system according to claim 7, characterized in that the swelling capability of the hydrogel is a function of temperature, wherein the swelling capability decreases with increasing temperature.

9. The implant system according to claim 8, characterized in that the swelling capability of the hydrogel decreases by at least 30% for a temperature increase of 10K.

10. The implant system according to claim 7, characterized in that the swelling capability of the hydrogel exhibits hysteresis.

11. The implant system according to claim 1, wherein a bonding agent is layered between the protective layer and base body.

* * * * *